(12) United States Patent
Dee et al.

(10) Patent No.: US 6,262,017 B1
(45) Date of Patent: Jul. 17, 2001

(54) PEPTIDES FOR ALTERING OSTEOBLAST ADHESION

(75) Inventors: Kay C. Dee, Troy; Thomas T. Andersen, Albany; Rena Bizios, Troy, all of NY (US)

(73) Assignee: Research Corporation Technologies, Inc., Tucson, AZ (US)

( * ) Notice: Subject to any disclaimer, the term of this patent is extended or adjusted under 35 U.S.C. 154(b) by 0 days.

(21) Appl. No.: 09/101,649

(22) PCT Filed: Jan. 15, 1997

(86) PCT No.: PCT/US97/00716

§ 371 Date: Jul. 14, 1998

§ 102(e) Date: Jul. 14, 1998

(87) PCT Pub. No.: WO97/25999

PCT Pub. Date: Jul. 24, 1997

Related U.S. Application Data

(60) Provisional application No. 60/010,026, filed on Jan. 16, 1996, and provisional application No. 60/029,189, filed on Oct. 31, 1996.

(51) Int. Cl.[7] .................................................. A61K 38/00
(52) U.S. Cl. .................. 514/2; 514/15; 514/16; 514/17; 514/18; 530/324; 530/325; 530/326; 530/327; 530/328; 530/329; 530/330; 623/11; 623/16
(58) Field of Search .................................. 514/2, 15–18; 530/324–330; 623/11, 16

(56) References Cited

U.S. PATENT DOCUMENTS

| | | | |
|---|---|---|---|
| 4,151,049 | 4/1979 | Janata | 204/1 T |
| 4,229,537 | 10/1980 | Hodgins et al. | 435/177 |
| 4,279,787 | 7/1981 | Huizinga | 260/8 |
| 4,411,832 | 10/1983 | Cuatrecasas et al. | 260/121 |
| 4,413,074 | 11/1983 | Wrasidlo et al. | 524/43 |
| 4,582,875 | 4/1986 | Ngo | 525/54.11 |
| 4,693,985 | 9/1987 | Degen et al. | 436/531 |
| 4,973,493 | 11/1990 | Guire | 427/2 |
| 5,171,271 | 12/1992 | Furcht et al. | 623/11 |
| 5,196,403 * | 3/1993 | Maraganore et al. | 514/12 |
| 5,198,423 | 3/1993 | Taguchi et al. | 514/12 |
| 5,229,490 * | 7/1993 | Tam | 530/324 |
| 5,294,551 * | 3/1994 | Furcht et al. | 435/402 |
| 5,324,819 | 6/1994 | Oppermann et al. | 530/350 |
| 5,354,557 | 10/1994 | Oppermann et al. | 424/423 |
| 5,371,191 | 12/1994 | Power et al. | 530/350 |
| 5,492,894 | 2/1996 | Bascom | 514/18 |
| 5,496,724 * | 3/1996 | Scarborough et al. | 435/252.3 |
| 5,753,617 * | 5/1998 | Heavner et al. | 514/9 |
| 5,777,083 * | 7/1998 | Burnie et al. | 530/387.3 |
| 5,932,545 * | 8/1999 | Henkin et al. | 514/13 |

FOREIGN PATENT DOCUMENTS

| | | |
|---|---|---|
| 266851 | 12/1990 | (CS) . |
| 54-16402 | 2/1979 | (JP) . |
| WO86/04334 | 7/1986 | (WO) . |
| WO91/05036 | 4/1991 | (WO) . |
| WO94/04676 | 3/1994 | (WO) . |
| 95/18665 | 7/1995 | (WO) . |

OTHER PUBLICATIONS

Cardin et al. "Molecular Modeling of Protein–Glycosaminoglycan Interactions" *Arteriosclerosis* 9, 21–32 (1989).

Puleo et al. "Mechanisms of fibronectin–mediated attachment of osteoblasts . . . " *Bone and Mineral* 18, 215–226 (1992).

Puleo et al. "RGDS Tetrapeptide Binds to Osteoblasts and Inhibits Fibronectin–Mediated Adhesion" *Bone* 12, 271–276 (1991).

Huebsch et al. "Endothelial Cell Interactions With Synthetic Peptides From The . . . " *Circ. Res.* 77, 43–53 (1995).

Wahl et al. "Synthetic fibronectin peptides suppress arthritis in rate by interrupting . . . " *J. Clin. Invest.* 94, 655–662 (1994).

Mann et al. "Delineation of the Glycosaminoglycan–binding Site in the Human Inflammatory . . . " *J. Biol. Chem.* 269, 23661–23667 (1994).

Lane et al. "Structural Requirements for the Neutralization of Heparin–like . . . " *J. Biol. Chem.* 262, 16343–16348 (1987).

Robinson et al. "Porous glass as a solid support for immobilisation or affinity . . . " *Biochim. Biophys. Acta* 242, 659–661 (1971).

Weetall "Preparation of Immobilized Proteins Covalently Coupled Through Silane Coupling . . . " *App. Biochem. Biotech.* 41, 157–188 (1993).

Baum et al. "Stability, Inhibition and Reactivation of Acetylcholinesterase . . . " *Biochim. Biophys. Acta* 268, 411–414 (1972).

Massia et al. "Human endothelial cell interactions with surface–coupled adhesion . . . " *J. Biomed. Materials Res.* 25, 223–242 (1991).

Multhaup "Identification and regulation of the high affinity binding site of the Alzheimer's . . . " *Biochimie* 76, 304–311 (1994).

(List continued on next page.)

Primary Examiner—Dwayne C. Jones
Assistant Examiner—C. Delacroix-Muirheid
(74) Attorney, Agent, or Firm—Heslin & Rothenberg, P.C.

(57) ABSTRACT

Peptides containing the amino acid sequence, $aa^1$-$aa^2$-$aa^3$-$aa^4$-$(Gly)_n$, devices for implantation coated with the peptides and methods for altering cell adhesion using the peptides are disclosed. The residues $aa^1$, $aa^2$, and $aa^4$ are independently Lys, Arg, Orn or, when the residue is N-terminal, Acp. The residue $aa^3$ is Ala, Gly, Val, Leu, Ile, Ser, Thr, Cys, Met, Asn, Nle, Nva or Abu. The preferred sequence is KRSR. Peptides containing cell adhesion-related sequences can be incorporated into or coated onto substrates to enhance osteoblast adhesion.

33 Claims, No Drawings

OTHER PUBLICATIONS

Zhou "Effects of a Bone Lysine–Rich 18 KDA Protein on Osteoblast–Like MC3T3–E1 Cells" *Biochem. Biophys. Res. Comm. 186*, 1288–1293 (1992).

Akiyama et al. "N–Hydroxy Amides. Synthesis and Properties of Linear and Cyclic Hexapeptides . . . " *J. Org. Chem. 53*, 6089–6094 (1988).

Kloszewiak et al. "Synthetic Peptides that Mimic the Binding Site of Horseshoe Crab . . . " *J. Infect. Dis. 143*, 1490–7 (1994).

A. Sette et al. "Structural Requirements for the Interaction Between Peptide . . . " *J. Immunol. 143*, 3289–94 (1989).

Schultz–Cherry et al., The Journal of Biol. Chem., vol. 270, No. 13, 7304–7310, 1995.*

Nishimoto et al., The Journal of Biol. Chem., vol. 266, No. 19, 12747–12751, 1991.*

CAPLUS DN–107:192315, Protter et al., WO 8702061, 1987, (abstract only).*

CAPLUS DN–98:107766, Damirov et al., Dokl. Akad. Nauk Az. SSR (1982), 38(6), 53–7 (abstract only).*

* cited by examiner

PEPTIDES FOR ALTERING OSTEOBLAST ADHESION

RELATED APPLICATION INFORMATION

This application claims the benefit of U.S. Provisional Application Nos. 60/010,026, filed Jan. 16, 1996 and 60/029,189, filed Oct. 31, 1996. Both Provisional Applications are incorporated herein by reference in their entirety.

FIELD OF THE INVENTION

The invention relates to peptides containing a cell adhesion-related amino acid sequence, and to devices and biomaterials for implantation coated with or incorporating peptides containing that sequence.

BACKGROUND OF THE INVENTION

Improved understanding of cellular and molecular events which occur at the interface between tissues and implants is beginning to allow new approaches to biomaterial design. The challenge is to produce biomaterials that are engineered to elicit specific, clinically-desirable responses from living cells and tissues in a patient's body. For example, it is clinically desirable for osteoblasts to rapidly deposit mineralized matrix on the surface of (or in close apposition to) newly implanted prostheses. The swift deposition of bone stabilizes the prosthesis and minimizes motion-induced damage to surgically traumatized tissue at the implantation site.

Anchorage-dependent cells (such as osteoblasts) must first adhere to a surface in order to perform subsequent cellular functions (e.g., proliferation, deposition of bone tissue, etc.). Since cell adhesion is the key to subsequent events, methods for promoting cell adhesion are of considerable interest. The effects on cell adhesion of peptides immobilized on the surfaces of substrates have been reported. Substrates have included polymers [Massia and Hubbell *Journal of Biomedical Materials* 25, 223–242 (1991)] and dental/orthopedic implant materials such as Cobalt-Chromium-Molybdenum alloy [Mikos et al. *Biomaterials for Cell and Drug Delivery* 331, 269–274 (1994)]. Adhesion-related peptides that have been attached to substrates have been mainly integrin-binding peptides, such as those which contain the Arginine-Glycine-Aspartic Acid (RGD) sequence.

The present invention relates to novel, heparin-binding, osteoblast-adhesive amino acid sequences of the formula:

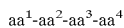

wherein:
  $aa^1$ represents the residue of an amino acid selected from the group consisting of H-Lys, H-Arg, H-Orn, and 6-aminocaproic acid (Acp);
  $aa^2$, and $aa^4$ independently represent the residue of an amino acid selected from the group consisting of lysine (Lys), arginine (Arg), and ornithine (Orn); and
  $aa^3$ represents the residue of an amino acid selected from the group consisting of alanine (Ala), glycine (Gly), valine (Val), leucine (Leu), isoleucine (Ile), serine (Ser), threonine (Thr), cysteine (Cys), methionine (Met), asparagine (Asn), norleucine (Nle), norvaline (Nva), and 2-aminobutyric acid (Abu). This peptide sequence has not been previously shown to exhibit any biological activity.

SUMMARY OF THE INVENTION

In one aspect, the invention relates to compounds of formulae

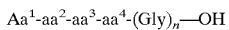

and

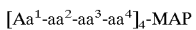

wherein:
  $Aa^1$ represents the residue of an amino acid selected from the group consisting of H-Lys, H-Arg, H-Orn, and 6-aminocaproic acid (Acp);
  $aa^2$, and $aa^4$ independently represent the residue of an amino acid selected from the group consisting of lysine (Lys), arginine (Arg), and ornithine (Orn);
  $aa^3$ represents the residue of an amino acid selected from the group consisting of alanine (Ala), glycine (Gly), valine (Val), leucine (Leu), isoleucine (Ile), serine (Ser), threonine (Thr) cysteine (Cys), methionine (Met), asparagine (Asn), norleucine (Nle), norvaline (Nva), and 2-aminobutyric acid (Abu); and n is zero or an integer from 1 to 6. The invention also includes pharmaceutically acceptable salts of the foregoing compounds. Under certain circumstances, discussed below, tetrapeptides of the following formulae are preferred: H-Lys-Arg-Met-Arg-OH (n=0 SEQ ID NO:12); H-Lys-Arg-Ala-Arg-OH (n=0 SEQ ID NO:19); H-Arg-Arg-Ser-Arg-OH (n=0 SEQ ID NO:26); H-Orn-Arg-Ser-Arg-OH (n=0 SEQ ID NO:33); H-Lys-Lys-Ser-Lys-OH (n=0 SEQ ID NO:40); H-Acp-Arg-Ser-Arg-OH (n=0 SEQ ID NO:47). The peptide sequence which is most preferred is H-Lys-Arg-Ser-Arg-OH (i.e. n=0 SEQ ID NO:1). The single-letter code for Lys-Arg-Ser-Arg is KRSR.

In another aspect, the invention relates to a device for implantation in an animal. The device comprises a substrate covalently attached to a peptide that includes the cell adhesion-related sequence and that has a molecular weight less than 4 kDa. The substrate may be a ceramic, a metal, a polymer, a polymer-coated or glass-coated metal or a composite. A preferred peptide has the formula H-Lys-Arg-Met-Arg-(Gly)$_3$—OH; H-Lys-Arg-Ala-Arg-(Gly)$_3$—OH; H-Arg-Arg-Ser-Arg-(Gly)$_3$—OH; H-Orn-Arg-Ser-Arg-(Gly)$_3$—OH; H-Lys-Lys-Ser-Lys-(Gly)$_3$—OH; or H-Acp-Arg-Ser-Arg-(Gly)$_3$—OH, with H-Lys-Arg-Ser-Arg-(Gly)$_3$—OH and [KRSR]$_4$-MAP being most preferred. The peptide may be attached to the substrate through a spacer chosen from the group consisting of poly(glycine), poly(alanine), poly(ethyleneimine), poly(lysine), hydroxyethylcellulose, poly(ethylene glycol), α,ω-alkylenediamines and ω-aminoalkanoic acids. A bone prosthetic device is a particularly preferred embodiment of the device aspect of the invention.

In another aspect, the invention relates to a method for enhancing the stabilization of an implant. According to the method, the implant is provided with a coating of a peptide of molecular weight less than 4 kDa incorporating the cell adhesion-related sequence. Preferably the coating of peptide is covalently attached to the implant. The preferred peptides are as above.

In a closely related aspect, the invention relates to a method for promoting the adhesion of osteoblasts to a prosthetic device. The method comprises providing a peptide of molecular weight less than 4 kDa incorporating the cell adhesion-related sequence at the surface of the prosthetic device. Preferred peptides are as above. The most preferred peptide is H-Lys-Arg-Ser-Arg-(Gly)$_n$—OH.

In yet another aspect, the invention relates to a method for disrupting cell adhesion. The method comprises bringing a cell into contact with a compound containing the cell adhesion-related peptide sequence at a concentration sufficient to inhibit cell adhesion.

In a closely related aspect, the invention relates to a method for treating a disease associated with cell adhesion. The method comprises administering to a mammal suffering from such a disease an amount of a compound containing the cell adhesion-related peptide sequence sufficient to inhibit cell adhesion.

In yet another aspect, the invention relates to a method of constructing a bone replacement or bone-reconstructive material. The method comprises preparing a biodegradable or inert polymer matrix which incorporates the cell adhesion-related peptide sequence, bringing osteoblasts into contact with the polymer matrix and adding growth factors.

DETAILED DESCRIPTION OF THE INVENTION

In the description that follows, certain conventions will be followed as regards the usage of terminology: The term "substrate" refers to the material that comprises the implant. This will commonly be a metal, such as titanium, or a polymer or a composite. The term "peptide", as it is commonly understood in the art, refers to a molecule of less than 10 kilodaltons (kDa) which is a polyamide of α-aminoacids. A "cell adhesion-related peptide"0 is a peptide that includes a sequence of the formula $Aa^1$-$aa^2$-$aa^3$-$aa^4$ wherein:

$Aa^1$ represents the residue of an amino acid selected from the group consisting of H-Lys, H-Arg, H-Orn. and 6-aminocaproic acid (Acp);

$aa^2$, and $aa^4$ independently represent the residue of an amino acid selected from the group consisting of lysine (Lys), arginine (Arg), and ornithine (Orn);

$aa^3$ represents the residue of an amino acid selected from the group consisting of alanine (Ala), glycine (Gly), valine (Val), leucine (Leu), isoleucine (Ile), serine (Ser), threonine (Thr), cysteine (Cys), methionine (Met), asparagine (Asn), norleucine (Nle), norvaline (Nva), and 2-aminobutyric acid (Abu). When the cell adhesion-related sequence occurs at the N-terminus of the peptide in which it resides, $aa^1$ may additionally be 6-aminocaproic acid. Thus, in such instances, $aa^1$ is written as $Aa^1$ and represents H-Lys, H-Arg, H-Orn, and Acp. The term "linker" refers to a molecule whose chemical reactivity is required to covalently join the substrate to the cell adhesion-related peptide, and which, as distinguished from an activating agent (such as a carbodiimide), leaves behind a residue that is incorporated in the substrate-peptide structure. Examples of linkers include aminoalkyltrialkoxysilanes for linking peptides to glass or titanium (via its surface oxide) and ethylene glycol diglycidyl ether (EGDGE) for linking cell-adhesion-related peptides (or spacers) to substrates having amino or hydroxyl functionalities on their surfaces. The term "spacer" refers to a molecule that is covalently attached to, and interposed between, the cell-adhesion-related peptide and the linker or substrate as an alternative to direct attachment of cell adhesion-related peptide to linker or substrate. Examples include poly(ethylene imine), α,ω-alkylenediamines, ω-aminoalkanoic acids and polypeptides not including the cell adhesion-related peptide sequence.

There may be an advantage to employing a spacer in that the spacer may provide the cell adhesion-related peptide sequence with some degree of mobility to allow it better access to the binding site on its target molecule; in this respect the spacer functions as a sort of tether between the cell adhesion-related peptide and the relatively rigid substrate. When the substrate provides an opportunity to bond to an aldehyde, poly(ethylene imine), ethylenediamine or any α,ω-alkylenediamine (e.g. hexamethylenediamine) can be employed as a spacer. Other spacers may be considered for other chemistries. When the substrate or linker provides an amino functionality, a polypeptide or ω-aminoalkanoic acid spacer can be employed. Examples include, but are not limited to: poly(glycine), poly(alanine), 8-aminooctanoic acid and even random polypeptides. In general, any difunctional molecule that can be attached at one of its termini to substrate or linker and at the other to the peptide will function in the invention, as long as the chemistry required for covalent attachment doesn't destroy the binding between the peptide and the target cell. Spacers that can be used in the invention include, in addition to those named above, polysilanes, polysiloxanes, hydroxyalkylcellulose, dextran, carboxymethylcellulose, poly(carboxymethylethylene imine), and polyvinyl alcohol.

It will be apparent that the process for inserting a spacer between the cell adhesion-related peptide and the substrate can be repeated several times. Subsequent applications of spacers may utilize additional functionalizable groups of the first spacer layer, as for example in hydroxyalkylcelluloses. In that case each successive binding thus involves increasing the number of spacer moieties, resulting in greater amounts of loading on the substrate surface.

Alternatively, a spacer having multiple side chain amines, such as poly(lysine), can be used to "amplify" the available surface functionalities. Multiple antigenic peptides (MAPs) typically consist of a branched lysine core matrix. The branched lysine core provides a scaffolding to support multiple copies of a particular peptide.

The peptide $[aa^1-aa^2-aa^3-aa^4]_4$-MAP, where four cell adhesion-related peptides are attached to a poly(lysine) MAP is such a molecule and can be described by the following formula:

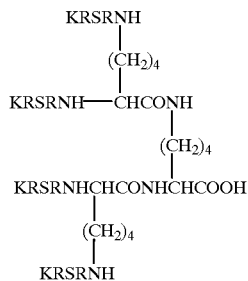

In the case where layers of hydrophilic spacers are covalently attached to a hydrophobic substrate, the nonspecific protein binding of the modified surface is lowered dramatically as compared to that of the virgin hydrophobic surface.

The terminology "providing the prosthetic device with a coating of a peptide" includes not only covalent attachment of the peptide to the surface of the device, but also adsorption and mechanical association. The important feature of the method requires that the cell adhesion-related peptide be associated with the surface of the device long enough to initiate adhesion of the osteoblasts and thereby to trigger subsequent cellular events. For this purpose, methods such as those described in U.S. Pat. No. 4,413,074 (detergent assisted adsorption); U.S. Pat. No. 4,151,049 (polymer swelling and mechanical entrapment); and U.S. Pat. No. 4,279,787 (crosslinking of an adsorbed layer) offer operable means for "providing the prosthetic device with a coating of a peptide". The pertinent portions of these disclosures are incorporated herein by reference.

The covalent binding of the surface ligand layers need not necessarily involve the intermediacy of a linker moiety although in certain cases, a linker is best employed. For covalent attachment of the cell adhesion-related peptide (or spacer and peptide) to the substrate, various chemistries and linkers are known, and the employment of a particular chemistry will depend in large measure upon the nature of the substrate, as will be clear to the person of skill in the art.

For example, when the device is titanium, the surface of the titanium device will, by virtue of exposure to the atmosphere, in fact be titanium oxide. Titanium oxide and silicon oxide surfaces can be rendered suitable for covalent attachment of peptides by treatment with aminoalkyltrialkoxysilanes, such as aminopropyltriethoxysilane. The use of aminoalkyltrialkylsilanes to derivatize glass is known in the art, and is described in some detail in the examples below. It provides the surface with reactive amino groups, to which peptides or spacers plus peptides can be attached. For other substrates, such as polyamides, the surface in its native form presents amino groups (see U.S. Pat. No. 4,693,985, which is incorporated herein by reference). In either case, the amino groups can be coupled with the carboxyl function of the cell adhesion-related peptide by procedures well known in the art, such as carbodiimides or EEDQ. The amino group can also be coupled with the amino group of peptides via glutaraldehyde or acid chlorides of dibasic acids (e.g. adipoyl chloride).

When the substrate presents a surface having free hydroxyls, the activated hydroxyls can also be reacted with nucleophiles (amines etc) via methods well known in the art. For example U.S. Pat. No. 4,582,875 describes activation with 2-fluoro-1-methylpyridinium tosylate and U.S. Pat. No. 4,229,537 describes activation with trichloro-s-triazine. The disclosures of both patents are incorporated herein by reference. It will be apparent to the person of skill that the attachment of a spacer having amino groups at both termini would then allow attachment of the cell adhesion-related peptide via its carboxyl function.

Substrates having free vicinal OH functionalities, such as found in cellulose, can be activated by any of the commonly known methods. See *Immobilized Affinity Peptide Techniques*, Greg T. Hermanson, A. Krisna Mallia, and Paul K. Smith Academic Press, Inc., San Diego Calif., (1992), p. 51–132, and *Affinity Chromatography, A Practical Approach*, Edited by P. D. G. Dean, W. S. Johnson and F. A. Middle, p. 31–59, IRL Press Ltd. Eynsham, Oxford OX81JJ, England (1987) and U.S. Pat. No. 3,389,142, the disclosures of which are incorporated herein by reference. Two preferred methods include cyanogen bromide activation and periodate activation.

Cyanogen bromide reacts with vicinal diols of cellulose to provide imidocarbonate and/or cyanate intermediates. These are highly activated toward nucleophilic attack and can be subsequently reacted with primary amines in the spacer or peptide. The result of the reaction is a peptide or spacer covalently attached to the cellulose through a carbamate. The activation reaction is carried out as described by Axen et al. [*Nature* 214, 1302–1304 (1967)] and Cuatrecasas et al. [*Proc. Nat. Acad. Sci. US* 61, 636–643 (1968)].

Periodate activation involves the periodate induced oxidative cleavage of vicinal diols to aldehydes, which are similarly reactive toward primary amines. A reduction step with sodium cyanoborohydride or similar reducing agent is commonly employed to convert the somewhat hydrolytically labile Schiff base to an alkylamine. These reactions are well known to persons of skill in the art and are described in detail in PCT application WO95/18665, pages 43–52 and 61–63, which are incorporated herein by reference.

To attach the oligopeptide to the spacer or linker, the C-terminal carboxylic acid residue of an N-protected peptide may be activated with a carbodiimide, such as 1-ethyl-3-(3-dimethylaminopropyl)carbodiimide (EDAC), and coupled with the amine-terminal spacer or linker. Alternatively, the coupling may be carried out with EEDQ (2-ethoxy-1-ethoxycarbonyl-1,2-dihydroquinoline) as described in WO95/18665. If desired, the N-terminal protection can then be cleaved by methods well-known in the art, although it does not appear necessary to do so. Alternatively, the unprotected peptide can be reacted with the linker or spacer. One such procedure is described below.

Aminoalkyltrialkoxysilanes (e.g. aminopropyltrimethoxysilane), ethylene glycol diglycidyl ether (EGDGE), 1,4-butanediol diglycidyl ether, epichlorohydrin, aliphatic dihalides, diacids, diacid halides, disulfonyl halides, and dialdehydes (e.g. glutaraldehyde) are preferred embodiments of the linker moiety.

A biomaterial employing cell adhesion-related peptides can be further enhanced by attaching integrin-binding peptides (such as RGD peptides). This allows one to utilize additional adhesion mechanisms of cells.

The cell adhesion-related peptide may be incorporated within a biomaterial, chemically immobilized on a biomaterial surface, or delivered in soluble form to a localized area in order to influence (i.e., to either enhance or to disrupt) the adhesion of cells (such as osteoblasts) or to regulate the presence, conformation, or activity of heparin-containing or heparin-like compounds.

Bone tissue may be engineered in vitro utilizing a biodegradable or inert polymer containing the cell adhesion-related peptide. A matrix or scaffold may be constructed from a polymer mesh of polyethylene terephthalate (PET) or polytetrafluoroethylene (PTFE), for example. The polymeric material is then hydroxylated according to methods known in the art and the cell adhesion-related peptide is coupled to the polymer using methods already described. Osteoblasts are then cultured with the mesh, and growth factors are added to promote cellular functions such as proliferation and deposition of bone.

The possible uses of a peptide that interacts with the heparin-like domain of a target glycoprotein include (but are not limited to) the mediation of blood coagulation, hypersensitivity reactions, proliferation of select cell types (such as vascular smooth muscle cells and fibroblasts), intimal hyperplasia, and angiogenesis.

Any suitable route of administration may be employed for providing the patient with an effective dosage of the cell adhesion-related peptide in soluble form. For example, oral, rectal, parenteral (subcutaneous, intramuscular, intravenous), transdermal, aerosol and like forms of administration may be employed. Dosage forms include tablets, troches, dispersions, suspensions, solutions, capsules, transdermal delivery systems, and the like. Methods for preparing the dosage forms are well known in the pharmaceutical art.

The pharmaceutical compositions of the present invention comprise the cell adhesion-related peptide as the active ingredient, or a pharmaceutically acceptable salt thereof, and may also contain a pharmaceutically acceptable carrier, and optionally, other therapeutic ingredients. The terms "pharmaceutically acceptable salts" or "a pharmaceutically acceptable salt thereof" refer to salts prepared from pharmaceutically acceptable non-toxic acids or bases. Suitable pharmaceutically acceptable acid addition salts for the compounds of the present invention include acetic, benzenesulfonic (besylate), benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic, and the like. Suitable pharmaceutically acceptable base addition salts include metal salts (e.g. aluminum, calcium, lithium, magnesium, potassium, sodium and zinc) or organic salts made from lysine, N,N'-dibenzylethylenediamine, chloroprocaine, choline, diethanolamine, ethylenediamine, meglumine(N-methylglucamine) and procaine. Sodium salts are preferred.

Pharmaceutical compositions of the present invention suitable for oral administration may be presented as discrete units such as capsules, cachets, or tablets, each containing a predetermined amount of the active ingredient, as a powder or granules, or as a solution or a suspension in an aqueous liquid, a non-aqueous liquid, an oil-in-water emulsion, or a water-in-oil liquid emulsion. Such compositions may be prepared by any of the methods of pharmacy, but all methods include the step of bringing into association the active ingredient with the carrier which constitutes one or more necessary ingredients. In general, the compositions are prepared by uniformly and intimately admixing the active ingredient with liquid carriers or finely divided solid carriers or both.

A series of tests described below demonstrate that not only is the cell adhesion-related sequence a novel osteoblast-adhesive peptide, but that one sequence in particular, the KRSR sequence is cell-adhesive via a molecular pathway which could not previously be selectively utilized at the peptide/amino acid level. Using standard protocols, 3-aminopropyltriethoxysilane was used to immobilize exposed amine groups on the surfaces of glass substrates, and 1-ethyl-3-(3dimethylaminopropyl)carbodimide was used to bind peptides having the sequence KRSRGGG (SEQ ID NO:4) to the exposed amine groups on the glass substrates.

Other glass substrates were modified with peptides having the sequence Lysine-Serine-Serine-Arginine-Glycine-Glycine-Glycine, or KSSRGGG (SEQ ID NO:10), as a control. Osteoblast adhesion on these surfaces was compared to osteoblast adhesion on (1) plain, unmodified glass substrates, (2) glass substrates which were treated with 3-aminopropyltriethoxysilane but were not modified with any peptides, (3) glass substrates modified with the cell-adhesive, integrin-binding peptide Arginine-Glycine-Aspartic Acid-Serine (RGDS) (SEQ ID NO:8), (4) glass substrates modified with the nonadhesive, control peptide Arginine-Aspartic Acid-Glycine-Serine (RDGS) (SEQ ID NO:9) and (5) glass substrates modified with a peptide having the sequence Histidine-Histidine-Tryptophan-Histidine (HHWH) (SEQ ID NO: 11) which represents another four amino acid sequence having a pattern of basic and neutral residues analogous to that of the peptides of the invention.

The results, presented in Table 1, establish the usefulness of the present invention and provide evidence that the KRSR (SEQ ID NO:1) active sequence is osteoblast-adhesive via a pathway which complements the integrin-binding pathway. Modification of surfaces with both RGD-containing peptides and the KRSR-containing peptides significantly enhanced osteoblast adhesion compared to adhesion on surfaces containing RGD peptides alone or on surfaces containing KRSR peptides alone.

TABLE 1

Osteoblast Four-Hour Adhesion

| Glass Treatment | Cell density; Cells/cm$^2$ | |
|---|---|---|
| | Average | SEM |
| None | 1552 | 176 |
| Aminophase | 1648 | 68 |
| RDGS (SEQ ID NO: 9) | 1656 | 105 |
| RGDS (SEQ ID NO: 8) | 1983* | 113 |
| KSSRGGG (SEQ ID NO: 10) | 1465 | 197 |
| KRSRGGG (SEQ ID NO: 4) | 2145** | 198 |
| RGDS + KRSRGGG | 2841** | 294 |

*significant at $p < 0.1$
**significant at $p < 0.05$

Evidence that the KRSR-containing peptide may selectively promote adhesion of other bone-related cells is provided by Tables 2, 3 and 4. The results, presented in Table 2, demonstrate that adhesion of bone marrow derived (BMD) osteoblast-like cells is also enhanced by modification of surfaces with the KRSR-containing peptides.

TABLE 2

Bone Marrow-Derived Osteoblast-like Cell Four-Hour Adhesion

| Glass Treatment | Cell density; Cells/cm$^2$ | |
|---|---|---|
| | Average | SEM |
| None | 897 | 176 |
| Aminophase | 1373 | 64.9 |
| RDGS (SEQ ID NO: 9) | 1712 | 86.6 |
| RGDS (SEQ ID NO: 8) | 1978 | 71.5 |
| KSSRGGG (SEQ ID NO: 10) | 1808 | 81 |
| KRSRGGG (SEQ ID NO: 4) | 2332* | 94.3 |

*significant at $p < 0.05$

Similarly, BMD osteoclasts (bone-resorbing cells) adhere to KRSRGGG-modified surfaces in greater numbers than to other treated or untreated surfaces (Table 3).

TABLE 3

Bone Marrow-Derived Osteoblast-like Cell Four-Hour Adhesion

| Glass Treatment | Cell density; Cells/cm$^2$ | |
|---|---|---|
| | Average | SEM |
| None | 1602 | 108 |
| Aminophase | 1813 | 94 |
| RDGS (SEQ ID NO: 9) | 2188 | 82.4 |
| RGDS (SEQ ID NO: 8) | 2241* | 85.3 |
| KSSRGGG (SEQ ID NO: 10) | 2090 | 96.8 |
| KRSRGGG (SEQ ID NO: 4) | 2377* | 73.6 |

*significant at $p < 0.05$

Non-bone related cells like fibroblasts and endothelial cells, however, do not adhere in significantly greater numbers to surfaces modified with the KRSR-containing peptide, as shown in Table 4 and 4a.

TABLE 4

Endothelial Cell Four-Hour Adhesion

| | Cell density; Cells/cm$^2$ | |
|---|---|---|
| Glass Treatment | Average | SEM |
| None | 1333 | 111.1 |
| Aminophase | 1544 | 179.7 |
| RDGS (SEQ ID NO: 9) | 1570 | 52.1 |
| RGDS (SEQ ID NO: 8) | 1913* | 104.4 |
| KSSRGGG (SEQ ID NO: 10) | 1483 | 92.7 |
| KRSRGGG (SEQ ID NO: 4) | 1600 | 92.7 |

*significant at $p < 0.05$

TABLE 4a

Fibroblast Four-Hour Adhesion

| | Cell density; Cells/cm$^2$ | |
|---|---|---|
| Glass Treatment | Average | SEM |
| None | 1010 | 73.7 |
| Aminophase | 1263 | 183.3 |
| RDGS (SEQ ID NO: 9) | 1037 | 62.9 |
| RGDS (SEQ ID NO: 8) | 1913 | 231.2 |
| KSSRGGG (SEQ ID NO: 10) | 1267 | 60.4 |
| KRSRGGG (SEQ ID NO: 4) | 1233 | 115 |

The effect on osteoblast adhesion of the KRSR-containing peptide was compared to a different peptide having a similar pattern of basic residues. As shown in Table 5, a significantly greater number of cells adhered to the KRSR peptide-modified substrate than to the HHWH peptide-modified substrate.

TABLE 5

Osteoblast Four-Hour Adhesion

| | Cell density; Cells/cm$^2$ | |
|---|---|---|
| Glass Treatment | Average | SEM |
| HHWH (SEQ ID NO: 12) | 1080 | 85 |
| KRSR (SEQ ID NO: 1) | 1508* | 135.2 |

*significant at $p < 0.01$

The KRSR peptides of different lengths were attached to the substrate and the effect on adhesion of osteoblasts was assessed. KRSR(4)-MAP indicates four residues of KRSR attached to the four primary amines of $H_2Lys(H_2Lys)LysOH$. Table 6 demonstrates that spacer length does not significantly affect osteoblast adhesion to KRSR-containing peptides.

TABLE 6

Osteoblast Four-Hour Adhesion

| | Cell density; Cells/cm$^2$ | |
|---|---|---|
| Glass Treatment | Average | SEM |
| KRSR (SEQ ID NO: 1) | 1508 | 135.2 |
| KRSRGGG (SEQ ID NO: 4) | 1770 | 185 |
| KRSRQGGGGG (SEQ ID NO: 7) | 1708 | 213.5 |
| KRSR(4)-MAP | 1923 | 133.1 |

Table 7 shows the results of pre-incubation of osteoblasts with either the RGDS-peptide, the KRSR-peptide or the KSSR-peptide prior to adhesion on KRSR peptide-modified substrate.

Pre-incubation of the osteoblasts with KRSR-containing peptide resulted in a significant decrease in adhesion to KRSR-modified substrate but adhesion was unaffected by pre-incubation with KSSR-containing peptide. Pre-incubating the osteoblasts with RGDS peptides did not significantly inhibit adhesion to KRSRGGG-modified substrates.

The effect of pre-incubation of BMD osteoblast-like and osteoclast-like cells was also examined with similar results (Tables 8 and 9).

TABLE 7

Calvarial Osteoblast Two-Hour Competitive Adhesion on KRSRGGG-Modified Substrates

| | Cell Adhesion expressed as % control Peptide concentration (mM) | | | | |
|---|---|---|---|---|---|
| Peptide | 0 | 0.5 | 1.0 | 1.5 | 2.0 |
| KRSRGGG (SEQ ID NO: 4) | 100 | 66.5 | 85.1 | 74.6 | 39.7 |
| KSSRGGG (SEQ ID NO: 10) | 100 | 77 | 88.6 | 130.6 | 123.6 |
| RGDS (SEQ ID NO: 8) | 100 | 80 | 82.6 | 93.9 | 111.3 |

TABLE 8

BMD Osteoblast-like Two-Hour Competitive Adhesion on KRSRGGG-Modified Substrates

| | Cell Adhesion expressed as % control Peptide concentration (mM) | | | | |
|---|---|---|---|---|---|
| Peptide | 0 | 0.5 | 1.0 | 1.5 | 2.0 |
| KRSRGGG (SEQ ID NO: 4) | 100 | 81.63 | 78.91 | 66.67 | 55.5 |
| KSSRGGG (SEQ ID NO: 10) | 100 | 109.52 | 93.65 | 101.59 | 107.94 |
| RGDS (SEQ ID NO: 8) | 100 | 96.2 | 87.2 | 89.7 | 87.2 |

TABLE 9

BMD Osteoclast-like Two-Hour Competitive Adhesion on KRSRGGG-Modified Substrates

| | Cell Adhesion expressed as % control Peptide concentration (mM) | | | | |
|---|---|---|---|---|---|
| Peptide | 0 | 0.5 | 1.0 | 1.5 | 2.0 |
| KRSRGGG (SEQ ID NO: 4) | 100 | 83.3 | 86.36 | 90.9 | 77.27 |
| KSSRGGG (SEQ ID NO: 10) | 100 | 84.37 | 101.56 | 92.18 | 93.75 |
| RGDS (SEQ ID NO: 8) | 100 | 106.27 | 114.08 | 109.39 | 104.7 |

Table 10 demonstrates that osteoblast adhesion is probably mediated by interaction between the peptide and heparan sulfate. The heparinase used degrades heparan sulfate in a very selective manner. Heparinase treatment significantly inhibited adhesion on KRSR peptide-containing substrate as well as on the control substrates (plain glass, aminophase glass, and KSSR peptide-modified substrate).

TABLE 10

Osteoblast Four-Hour Adhesion
in the Absence and Presence of 0.2 U/ml Heparinase

| | Cell density; Cells/cm$^2$) Heparinase | | | |
|---|---|---|---|---|
| | none | | 0.2 U/ml | |
| Glass Treatment | Average | SEM | Average | SEM |
| None | 1552 | 176 | 503 | 43 |
| Aminophase | 1648 | 68 | 378 | 54 |
| RDGS (SEQ ID NO: 9) | 1656 | 105 | 378 | 45 |
| RGDS (SEQ ID NO: 8) | 1983 | 113 | 470 | 57 |
| KSSRGGG (SEQ ID NO: 10) | 1465 | 197 | 540 | 88 |
| KRSRGGG (SEQ ID NO: 4) | 2145 | 198 | 330 | 35 |

These results demonstrate the feasibility of using the amino acid sequence Lysine-Arginine-Serine-Arginine (KRSR (SEQ ID NO:1)) to interact with cell-membrane heparin sulfate proteoglycans of osteoblasts or of other cell types in order to influence cell adhesion.

Peptides were synthesized on a BioSearch 9500 automated peptide synthesizer using a Merrifield resin and either Fmoc strategy, for the Fmoc-protected RGDS (SEQ ID NO:8), or tBOC strategy for all other peptides. Hydrofluoric acid cleavage was performed with the "low-high" method [Tam et al., *J. Am. Chem. Soc.* 103, 6442–6455 (1983)] and the peptides were purified using reverse phase chromatography on a Sep-Pak cartridge (Millipore, Bedford, Mass.) followed by HPLC chromatography (C18 column, gradient 0–60% acetonitrile and 0.1% trifluoroacetic acid). Purified peptides were examined by amino acid analysis to confirm composition and purity, as well as by automated gas phase sequence analysis to confirm amino acid sequences.

Peptides were immobilized on substrate surfaces (borosilicate glass, 18 mm round coverslips; Fisher) using silane coupling techniques adapted from published protocols [Weetall *Applied Biochem. Biotech.* 41, 158–188 (1993); Robinson et al. *Biochim. Biophys. Acta* 242, 659–661 (1971); and Baum et al. *Biochim. Biophys. Acta* 268, 411–414 (1972)], the disclosures of which are incorporated herein by reference. Briefly, 3-aminopropyltriethoxysilane (Sigma) was allowed to react with hydroxyl groups on the material surfaces to produce "aminophase" substrates. Incubation of aminophase substrates with a solution of a given peptide, 1-ethyl-3-(3-dimethylaminopropyl)carbodiimide (Sigma), and N-ethyl morpholine (Sigma) resulted in immobilization of the peptide.

In preparing for peptide immobilization, borosilicate glass coverslips (Fisher) were etched for one hour in a 3:1 (v/v) solution of 2 N sulfuric acid and 2 N nitric acid, degreased in acetone and ethanol, and rinsed with distilled water. The degreased and acid-etched substrates were placed in glass petri dishes which had been previously cleaned with a 3.5% solution of 30% hydrogen peroxide in 18 M sulfuric acid.

The substrates were dried at 160° C. for at least one hour, rinsed with dry acetone, and immersed in 2% 3-aminopropyltriethoxysilane in dry acetone, supplemented with 2% triethylamine under an argon atmosphere at 400° C. for one hour. The substrates were rinsed (under an argon atmosphere) once with methylene chloride and twice with dry acetone, and cured under argon at 120° C. for three hours. At this stage, the silane-coated substrates possessed exposed amine groups and were, thus, classified as "aminophase" substrates.

Peptides were covalently bound to immobilized exposed amine groups on the substrate surfaces during a twenty-minute incubation (under argon) with a 25:25:1 (v/v/v) solution of peptide (0.1 mM in dry N,N-dimethylformamide): 1-ethyl-3-(3-dimethylaminopropyl) carbodiimide (2.5 mg/mL in dry N,N-dimethylformamide): n-ethylmorpholine. Unreacted amine groups were passivated by soaking peptide-modified substrates in acetic anhydride for 5 minutes; absorbed peptides were then removed by soaking for 5 minutes in 4 M urea, rinsing in distilled water, and soaking for 5 minutes in 1 M sodium chloride. Peptide-modified substrates were then thoroughly rinsed in distilled water prior to sterilization and use.

In all experiments performed in the present invention, substrates which had been aminated but not peptide-grafted (i.e., aminophase substrates) were used as controls. Substrates which had been etched in a 3:1 (v/v) solution of 2 N sulfuric acid: 2 N nitric acid, degreased in acetone and ethanol, and rinsed copiously with distilled water were used as references. Glass substrates were sterilized via overnight ultraviolet irradiation prior to use in experiments.

As can be seen from Table 1, the substrates having the KRSR (SEQ ID NO:1) active sequence and those having the RGDS (SEQ ID NO:8) plus KRSR showed statistically significant osteoblast adhesion. Moreover, the osteoblast adhesion via KRSR appears to complement the enhanced adhesion on surfaces modified with the integrin-binding peptide RGDS.

Titanium and titanium alloys (for example, Ti-6Al—V) are often used in dental and orthopedic implants. It is known that within approximately one second of exposure to air, a surface oxide layer (approximately a few nanometers thick) forms on the surface of titanium and titanium alloys. From surface characterization techniques such as X-ray photoemission spectroscopy, auger electron spectroscopy, and secondary ion mass spectroscopy, it has been determined that the oxide layers on commercial samples are primarily composed of $TiO_2$, with small amounts of the suboxides $Ti_2O_3$ and TiO present at the metal/surface oxide interface.

The stable $TiO_2$ oxide layer on titanium and Ti-6Al-4V samples comprises a surface which can be modified with immobilized peptides via the same silanization techniques used on glass ($SiO_2$) surfaces. In the present study, medical grade Ti-6Al-4V stock (ASTM F-136; Osteonics) was sectioned into coupons using a low-speed saw equipped with a diamond wafering blade. The metal coupons were then polished to a 30 micron finish via sanding (using 600 grit paper on a sanding wheel), polishing to a 15 micron finish and then to a 9 micron finish (using diamond spray on a polishing wheel), and finally polishing to a 3 micron finish using aluminum oxide ($Al_2O_3$) mixed with 30% hydrogen peroxide on a polishing wheel), according to standard techniques. Polished metal coupons were degreased with acetone and ethanol and rinsed copiously with distilled water before peptides were immobilized on the metal surfaces (via the aforementioned techniques). Osteoblasts cultured for two weeks on unmodified Ti-6-Al-4V, aminated Ti-6Al-4V, RDGS-modified Ti-6Al-4V, and RGDS-modified Ti-6Al-4V exhibited normal morphology and cytoskeletal organization on all substrates tested. In analogous fashion it is anticipated that cell adhesion-related peptides can be similarly immobilized on titanium substrates.

While the specific embodiment of the invention has been shown and described in detail to illustrate the application of the principles of the invention, it will be understood that the invention may be embodied otherwise without departing from such principles.

What is claimed is:

1. A compound of formula

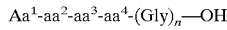

wherein:

$Aa^1$ represents the residue of an amino acid selected from the group consisting of H-Lys, H-Arg, H-Orn and 6-aminocaproic acid (Acp);

$aa^2$, and $aa^4$ independently represent the residue of an amino acid selected from the group consisting of lysine (Lys), arginine (Arg), and ornithine (Orn);

$aa^3$ represents the residue of an amino acid selected from the group consisting of alanine (Ala), glycine (Gly), valine (Val), leucine (Leu), isoleucine (Ile), serine (Ser), threonine (Thr), cysteine (Cys), methionine (Met), asparagine (Asn), norleucine (Nle), norvaline (Nva), and 2-aminobutyric acid (Abu); and n is an integer from 1 to 6;

or pharmaceutically acceptable salt thereof.

2. A compound according to claim 1 of formula

H-Lys-Arg-Ser-Arg-(Gly)$_n$—OH (n=0 SEQ ID NO:1; n=1 SEQ ID NO:2; n=2 SEQ ID NO:3; n=3 SEQ ID NO:4; n=4 SEQ ID NO:5; n=5 SEQ ID NO:6; n=6 SEQ ID NO:7), H-Lys-Arg-Met-Arg-(Gly)$_n$—OH (n=0 SEQ ID NO:12; n=1 SEQ ID NO:13; n=2 SEQ ID NO:14; n=3 SEQ ID NO:15; n=4 SEQ ID NO:16; n=5 SEQ ID NO:17; n=6 SEQ ID NO:18), H-Lys-Arg-Ala-Arg-(Gly)$_n$—OH (n=0 SEQ ID NO:19; n=1 SEQ ID NO:20; n=2 SEQ ID NO:21; n=3 SEQ ID NO:22; n=4 SEQ ID NO:23; n=5 SEQ ID NO:24; n=6 SEQ ID NO:25), H-Arg-Arg-Ser-Arg-(Gly)$_n$—OH (n=0 SEQ ID NO:26; n=1 SEQ ID NO:27; n=2 SEQ ID NO:28; n=3 SEQ ID NO:29; n=4 SEQ ID NO:30; n=5 SEQ ID NO:31; n=6 SEQ ID NO:32), H-Orn-Arg-Ser-Arg-(Gly)$_n$—OH (n=0 SEQ ID NO:33; n=1 SEQ ID NO:34; n=2 SEQ ID NO:35; n=3 SEQ ID NO:36; n=4 SEQ ID NO:37; n=5 SEQ ID NO:38; n=6 SEQ ID NO:39), H-Lys-Lys-Ser-Lys-(Gly)$_n$—OH (n=0 SEQ ID NO:40; n=1 SEQ ID NO:41; n=2 SEQ ID NO:42; n=3 SEQ ID NO:43; n=4 SEQ ID NO:44; n=5 SEQ ID NO:45; n=6 SEQ ID NO:46), or H-Acp-Arg-Ser-Arg-(Gly)$_n$—OH (n=0 SEQ ID NO:47; n=1 SEQ ID NO:48; n=2 SEQ ID NO:49; n=3 SEQ ID NO:50; n=4 SEQ ID NO:51; n=5 SEQ ID NO:52; n=6 SEQ ID NO:53).

3. A compound according to claim 2 of formula

H-Lys-Arg-Ser-Arg-(Gly)$_n$—OH (n=0 SEQ ID NO:1; n=1 SEQ ID NO:2; n=2 SEQ ID NO:3; n=3 SEQ ID NO:4; n=4 SEQ ID NO:5; n=5 SEQ ID NO:6; n=6 SEQ ID NO:7).

4. A method for disrupting cell adhesion comprising bringing a cell into contact with a concentration of compound according to claim 1 sufficient to inhibit cell adhesion.

5. A method for treating a disease resulting from dysfunctional cell adhesion comprising administering to a mammal suffering from said disease an amount of a compound according to claim 1 sufficient to inhibit cell adhesion.

6. A method of constructing a bone replacement or bone-reconstructive material, comprising preparing a biodegradable polymer matrix which incorporates the compounds of claim 1, and allowing osteoblasts into contact with the polymer matrix.

7. A compound of formula [KRSR]$_4$-MAP.

8. A device for implantation in an animal comprising a substrate covalently attached to a peptide of molecular weight less than 4 kDa, other than SPPRRARVT said peptide incorporating a sequence of the formula

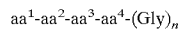

wherein:

$aa^1$ represents the residue of an amino acid selected from the group consisting of lysine (Lys), arginine (Arg), ornithine (Orn) and, when $aa^1$ is at the N-terminus, 6-aminocaproic acid (Acp);

$aa^2$, and $aa^4$ independently represent the residue of an amino acid selected from the group consisting of lysine (Lys), arginine (Arg), and ornithine (Orn);

$aa^3$ represents the residue of an amino acid selected from the group consisting of alanine (Ala), glycine (Gly), valine (Val), leucine (Leu), isoleucine (Ile), serine (Ser), threonine (Thr), cysteine (Cys), methionine (Met) asparagine (Asn), norleucine (Nle), norvaline (Nva), and 2-aminobutyric acid (Abu); and n is zero or an integer from 1 to 6.

9. A device according to claim 8 comprising a substrate covalently attached to a peptide incorporating a sequence selected from the group consisting of Lys-Arg-Ser-Arg-(Gly)$_n$ (n=0 SEQ ID NO:1; n=1 SEQ ID NO:2; n=2 SEQ ID NO:3; n=3 SEQ ID NO:4; n=4 SEQ ID NO:5; n=5 SEQ ID NO:6; n=6 SEQ ID NO:7), Lys-Arg-Met-Arg-(Gly)$_n$ (n=0 SEQ ID NO:12; n=1 SEQ ID NO:13; n=2 SEQ ID NO:14; n=3 SEQ ID NO:15; n=4 SEQ ID NO:16; n=5 SEQ ID NO:17; n=6 SEQ ID NO:18), Lys-Arg-Ala-Arg-(Gly)$_n$ (n=0

SEQ ID NO:19; n=1 SEQ ID NO:20; n=2 SEQ ID NO:21; n=3 SEQ ID NO:22; n=4 SEQ ID NO:23; n=5 SEQ ID NO:24; n=6 SEQ ID NO:25), Arg-Arg-Ser-Arg-(Gly)$_n$ (n=0 SEQ ID NO:26; n=1 SEQ ID NO:27; n=2 SEQ ID NO:28; n=3 SEQ ID NO:29; n=4 SEQ ID NO:30; n=5 SEQ ID NO:31; n=6 SEQ ID NO:32), Orn-Arg-Ser-Arg-(Gly)$_n$ (n=0 SEQ ID NO:33; n=1 SEQ ID NO:34; n=2 SEQ ID NO:35; n=3 SEQ ID NO:36; n=4 SEQ ID NO:37; n=5 SEQ ID NO:38; n=6 SEQ ID NO:39), Lys-Lys-Ser-Lys-(Gly)$_n$ (n=0 SEQ ID NO:40; n=1 SEQ ID NO:41; n=2 SEQ ID NO:42; n=3 SEQ ID NO:43; n=4 SEQ ID NO:44; n=5 SEQ ID NO:45; n=6 SEQ ID NO:46), and Acp-Arg-Ser-Arg-(Gly)$_n$ (n=0 SEQ ID NO:47; n=1 SEQ ID NO:48; n=2 SEQ ID NO:49; n=3 SEQ ID NO:50; n=4 SEQ ID NO:51; n=5 SEQ ID NO:52; n=6 SEQ ID NO:53).

10. A device according to claim 8 wherein said peptide of molecular weight less than 4 kDa has the formula $$\text{H-Lys-Arg-Ser-Arg-(Gly)}_n\text{—OH}$$

(n=0 SEQ ID NO:1; n=1 SEQ ID NO:2; n=2 SEQ ID NO:3; n=3 SEQ ID NO:4; n=4 SEQ ID NO:5; n=5 SEQ ID NO:6; n=6 SEQ ID NO:7).

11. A device according to claim 8 wherein said peptide incorporates the sequence KRSR (SEQ ID NO:1).

12. A device according to claim 11 wherein said peptide incorporating the sequence KRSR is [KRSR]$_4$-MAP.

13. A device for according to claim 8 wherein said substrate is chosen from the group consisting of ceramics, metals, polymers and composites.

14. A bone prosthetic device according to claim 8.

15. A method for enhancing the stabilization of an implant comprising providing said implant with a coating of a peptide of molecular weight less than 4 kDa, other than SPPRRARVT said peptide incorporating the sequence of the formula $$aa^1\text{-}aa^2\text{-}aa^3\text{-}aa^4\text{-(Gly)}_n$$

wherein:
aa$^1$ represents the residue of an amino acid selected from the group consisting of lysine (Lys), arginine (Arg), ornithine (Orn) and, when aa$^1$ is at the N-terminus, 6-aminocaproic acid (Acp);
aa$^2$, and aa$^4$ independently represent the residue of an amino acid selected from the group consisting of lysine (Lys), arginine (Arg), and ornithine (Orn);
aa$^3$ represents the residue of an amino acid selected from the group consisting of alanine (Ala), glycine (Gly), valine (Val), leucine (Leu), isoleucine (Ile), serine (Ser), threonine (Thr), cysteine (Cys), methionine (Met) asparagine (Asn), norleucine (Nle), norvaline (Nva), and 2-aminobutyric acid (Abu); and
n is zero or an integer from 1 to 6.

16. A bone replacement or bone-reconstructive material, comprising a polymer matrix and a peptide of molecular weight less than 4 kDa, other than SPPRRARVT said peptide incorporating a sequence of the formula $$aa^1\text{-}aa^2\text{-}aa^3\text{-}aa^4\text{-(Gly)}_n$$

wherein:
aa$^1$ represents the residue of an amino acid selected from the group consisting of lysine (Lys), arginine (Arg), ornithine (Orn) and, when aa$^1$ is at the N-terminus, 6-aminocaproic acid (Acp);
aa$^2$, and aa$^4$ independently represent the residue of an amino acid selected from the group consisting of lysine (Lys), arginine (Arg), and ornithine (Orn);
aa$^3$ represents the residue of an amino acid selected from the group consisting of alanine (Ala), glycine (Gly), valine (Val), leucine (Leu), isoleucine (Ile), serine (Ser), threonine (Thr), cysteine (Cys), methionine (Met) asparagine (Asn), norleucine (Nle), norvaline (Nva), and 2-aminobutyric acid (Abu); and
n is zero or an integer from 1 to 6.

17. A bone replacement or bone-reconstructive material according to claim 16 wherein said peptide incorporates a sequence selected from the group consisting of Lys-Arg-Ser-Arg-(Gly)$_n$ (n=0 SEQ ID NO:1; n=1 SEQ ID NO:2; n=2 SEQ ID NO:3; n=3 SEQ ID NO:4; n=4 SEQ ID NO:5; n=5 SEQ ID NO:6; n=6 SEQ ID NO:7), Lys-Arg-Met-Arg-(Gly)$_n$ (n=0 SEQ ID NO:12; n=1 SEQ ID NO:13; n=2 SEQ ID NO:14; n=3 SEQ ID NO:15; n=4 SEQ ID NO:16; n=5 SEQ ID NO:17; n=6 SEQ ID NO:18), Lys-Arg-Ala-Arg-(Gly)$_n$ (n=0 SEQ ID NO:19; n=1 SEQ ID NO:20; n=2 SEQ ID NO:21; n=3 SEQ ID NO:22; n=4 SEQ ID NO:23; n=5 SEQ ID NO:24; n=6 SEQ ID NO:25), Arg-Arg-Ser-Arg-(Gly)$_n$ (n=0 SEQ ID NO:26; n=1 SEQ ID NO:27; n=2 SEQ ID NO:28; n=3 SEQ ID NO:29; n=4 SEQ ID NO:30; n=5 SEQ ID NO:31; n=6 SEQ ID NO:32), Orn-Arg-Ser-Arg-(Gly)$_n$ (n=0 SEQ ID NO:33; n=1 SEQ ID NO:34; n=2 SEQ ID NO:35; n=3 SEQ ID NO:36; n=4 SEQ ID NO:37; n=5 SEQ ID NO:38; n=6 SEQ ID NO:39), Lys-Lys-Ser-Lys-(Gly)$_n$ (n=0 SEQ ID NO:40; n=1 SEQ ID NO:41; n=2 SEQ ID NO:42; n=3 SEQ ID NO:43; n=4 SEQ ID NO:44; n=5 SEQ ID NO:45; n=6 SEQ ID NO:46), or Acp-Arg-Ser-Arg-(Gly)$_n$ (n=0 SEQ ID NO:47; n=1 SEQ ID NO:48; n=2 SEQ ID NO:49; n=3 SEQ ID NO:50; n=4 SEQ ID NO:51; n=5 SEQ ID NO:52; n=6 SEQ ID NO:53).

18. A bone replacement or bone-reconstructive material according to claim 17 wherein said polymer is biodegradable.

19. A bone replacement or bone-reconstructive material according to claim 17 wherein said polymer is inert.

20. A bone replacement or bone-reconstructive material according to claim 16 wherein said polymer is biodegradable.

21. A bone replacement or bone-reconstructive material according to claim 16 wherein said polymer is inert.

22. A method for disrupting cell adhesion comprising bringing a cell into contact with a cell adhesion inhibiting concentration of a peptide of molecular weight less than 4 kDa, said peptide incorporating a sequence of the formula $$aa^1\text{-}aa^2\text{-}aa^3\text{-}aa^4\text{-(Gly)}_n$$

wherein:
aa$^1$ represents the residue of an amino acid selected from the group consisting of lysine (Lys), arginine (Arg), ornithine (Orn) and, when aa$^1$ is at the N-terminus, 6-aminocaproic acid (Aep);
aa$^2$, and aa$^4$ independently represent the residue of an amino acid selected from the group consisting of lysine (Lys), arginine (Arg), and ornithine (Orn) covalently bonded only at their α-aminoacid functionalities;
aa$^3$ represents the residue of an amino acid selected from the group consisting of alanine (Ala), glycine (Gly), valine (Val), leucine (Leu), isoleucine (Ile), serine (Ser), threonine (Thr), cysteine (Cys), methionine (Met) asparagine (Asn), norleucine (Nle), norvaline (Nva), and 2-aminobutyric acid (Abu); and
n is zero or an integer from 1 to 6.

23. A method for disrupting cell adhesion according to claim 22 wherein said peptide incorporates a sequence selected from the group consisting of Lys-Arg-Ser-Arg- (Gly)$_n$ (n=0 SEQ ID NO:1; n=1 SEQ ID NO:2; n=2 SEQ ID NO:3; n=3 SEQ ID NO:4; n=4 SEQ ID NO:5; n=5 SEQ ID NO:6; n=6 SEQ ID NO:7), Lys-Arg-Met-Arg-(Gly)$_n$ (n=0 SEQ ID NO:12; n=1 SEQ ID NO:13; n=2 SEQ ID NO:14; n=3 SEQ ID NO:15; n=4 SEQ ID NO:16; n=5 SEQ ID NO:17; n=6 SEQ ID NO:18), Lys-Arg-Ala-Arg-(Gly)$_n$ (n=0 SEQ ID NO:19; n=1 SEQ ID NO:20; n=2 SEQ ID NO:21; n=3 SEQ ID NO:22; n=4 SEQ ID NO:23; n=5 SEQ ID NO:24; n=6 SEQ ID NO:25), Arg-Arg-Ser-Arg-(Gly)$_n$ (n=0 SEQ ID NO:26; n=1 SEQ ID NO:27; n=2 SEQ ID NO:28; n=3 SEQ ID NO:29; n=4 SEQ ID NO:30; n=5 SEQ ID NO:31; n=6 SEQ ID NO:32), Orn-Arg-Ser-Arg-(Gly)$_n$ (n=0 SEQ ID NO:33; n=1 SEQ ID NO:34; n=2 SEQ ID NO:35; n=3 SEQ ID NO:36; n=4 SEQ ID NO:37; n=5 SEQ ID NO:38; n=6 SEQ ID NO:39), Lys-Lys-Ser-Lys-(Gly)$_n$ (n=0 SEQ ID NO:40; n=1 SEQ ID NO:41; n=2 SEQ ID NO:42; n=3 SEQ ID NO:43; n=4 SEQ ID NO:44; n=5 SEQ ID NO:45; n=6 SEQ ID NO:46), Acp-Arg-Ser-Arg-(Gly)$_n$ (n=0 SEQ ID NO:47; n=1 SEQ ID NO:48; n=2 SEQ ID NO:49; n=3 SEQ ID NO:50; n=4 SEQ ID NO:51; n=5 SEQ ID NO:52; n=6 SEQ ID NO:53).

24. A method for disrupting angiogenesis comprising allowing a cell to contact a cell adhesion inhibiting concentration of a peptide of molecular weight less than 4 kDa, said peptide incorporating a sequence of the formula $$aa^1\text{-}aa^2\text{-}aa^3\text{-}aa^4\text{-}(Gly)_n$$

wherein:
aa$^1$ represents the residue of an amino acid selected from the group consisting of lysine (Lys), arginine (Arg), ornithine (Orn) and, when aa$^1$ is at the N-terminus, 6-aminocaproic acid (Acp);
aa$^2$, and aa$^4$ independently represent the residue of an amino acid selected from the group consisting of lysine (Lys), arginine (Arg), and ornithine (Orn), covalently bonded only at their α-aminoacid functionalities;
aa$^3$ represents the residue of an amino acid selected from the group consisting of alanine (Ala), glycine (Gly), valine (Val), leucine (Leu), isoleucine (Ile), serine (Ser), threonine (Thr), cysteine (Cys), methionine (Met) asparagine (Asn), norleucine (Nle), norvaline (Nva), and 2-aminobutyric acid (Abu); and
n is zero or an integer from 1 to 6.

25. A method for disrupting angiogenesis according to claim 24 wherein said peptide incorporates a sequence selected from the group consisting of Lys-Arg-Ser-Arg-(Gly)$_n$ (n=0 SEQ ID NO:1; n=1 SEQ ID NO:2; n=2 SEQ ID NO:3; n=3 SEQ ID NO:4; n=4 SEQ ID NO:5; n=5 SEQ ID NO:6; n=6 SEQ ID NO:7), Lys-Arg-Met-Arg-(Gly)$_n$ (n=0 SEQ ID NO:12; n=1 SEQ ID NO:13; n=2 SEQ ID NO:14; n=3 SEQ ID NO:15; n=4 SEQ ID NO:16; n=5 SEQ ID NO:17; n=6 SEQ ID NO:18), Lys-Arg-Ala-Arg-(Gly)$_n$ (n=0 SEQ ID NO:19; n=1 SEQ ID NO:20; n=2 SEQ ID NO:21; n=3 SEQ ID NO:22; n=4 SEQ ID NO:23; n=5 SEQ ID NO:24; n=6 SEQ ID NO:25), Arg-Arg-Ser-Arg-(Gly)$_n$ (n=0 SEQ ID NO:26; n=1 SEQ ID NO:27; n=2 SEQ ID NO:28; n=3 SEQ ID NO:29; n=4 SEQ ID NO:30; n=5 SEQ ID NO:31; n=6 SEQ ID NO:32), Orn-Arg-Ser-Arg-(Gly)$_n$ (n=0 SEQ ID NO:33; n=1 SEQ ID NO:34; n=2 SEQ ID NO:35; n=3 SEQ ID NO:36; n=4 SEQ ID NO:37; n=5 SEQ ID NO:38; n=6 SEQ ID NO:39), Lys-Lys-Ser-Lys-(Gly)$_n$ (n=0 SEQ ID NO:40; n=1 SEQ ID NO:41; n=2 SEQ ID NO:42; n=3 SEQ ID NO:43; n=4 SEQ ID NO:44; n=5 SEQ ID NO:45; n=6 SEQ ID NO:46), Acp-Arg-Ser-Arg-(Gly)$_n$ (n=0 SEQ ID NO:47; n=1 SEQ ID NO:48; n=2 SEQ ID NO:49; n=3 SEQ ID NO:50; n=4 SEQ ID NO:51; n=5 SEQ ID NO:52; n=6 SEQ ID NO:53).

26. A method or treating a disease resulting from dysfunctional cell adhesion comprising administering to a mammal suffering from said disease a therapeutically effective amount of a peptide of molecular weight less than 4 kDa, said peptide incorporating a sequence of the formula $$aa^1\text{-}aa^2\text{-}aa^3\text{-}aa^4\text{-}(Gly)_n$$

wherein:
aa$^1$ represents the residue of an amino acid selected from the group consisting of lysinc (Lys), argirine (Arg), ornithine (Orn) and, when aa$^1$ is at the N-terminus, 6-aminocaproic acid (Acp);
aa$^2$, and aa$^4$ independently represent the residue of an amino acid selected from the group consisting of lysine (Lys), arginine (Arg), and ornithine (Orn), covalently bonded only at their α-aminoacid functionalities;
aa$^3$ represents the residue of an amino acid selected from the group consisting of alanine (Ala), glycine (Gly), valine (Val), leucine (Lcu), isoleucine (Ile), serine (Ser), threonine (Thr), cysteine (Cys), methioninc (Met) asparagine (Asn), norleucine (Nlc), norvaline (Nva), and 2-aminobutyric acid (Abu); and
n is zero or an integer from 1 to 6.

27. A method for treating a disease resulting from dysfunctional cell adhesion according to claim 26 wherein said peptide incorporates a sequence selected from the group consisting of Lys-Arg-Ser-Arg-(Gly)$_n$ (n=0 SEQ ID NO:1; n=1 SEQ ID NO:2; n=2 SEQ ID NO:3; n=3 SEQ ID NO:4; n=4 SEQ ID NO:5; n=5 SEQ ID NO:6; n=6 SEQ ID NO:7), Lys-Arg-Met-Arg-(Gly)$_n$ (n=0 SEQ ID NO:12; n=1 SEQ ID NO:13; n=2 SEQ ID NO:14; n=3 SEQ ID NO:15; n=4 SEQ ID NO:16; n=5 SEQ ID NO:17; n=6 SEQ ID NO:18), Lys-Arg-Ala-Arg-(Gly)$_n$ (n=0 SEQ ID NO:19; n=1 SEQ ID NO:20; n=2 SEQ ID NO:21; n=3 SEQ ID NO:22; n=4 SEQ ID NO:23; n=5 SEQ ID NO:24; n=6 SEQ ID NO:25), Arg-Arg-Ser-Arg-(Gly)$_n$ (n=0 SEQ ID NO:26; n=1 SEQ ID NO:27; n=2 SEQ ID NO:28; n=3 SEQ ID NO:29; n=4 SEQ ID NO:30; n=5 SEQ ID NO:31; n=6 SEQ ID NO:32), Orn-Arg-Ser-Arg-(Gly)$_n$ (n=0 SEQ ID NO:33; n=1 SEQ ID NO:34; n=2 SEQ ID NO:35; n=3 SEQ ID NO:36; n=4 SEQ ID NO:37; n=5 SEQ ID NO:38; n=6 SEQ ID NO:39), Lys-Lys-Ser-Lys-(Gly)$_n$ (n=0 SEQ ID NO:40; n=1 SEQ ID NO:41; n=2 SEQ ID NO:42; n=3 SEQ ID NO:43; n=4 SEQ ID NO:44; n=5 SEQ ID NO:45; n=6 SEQ ID NO:46), Acp-Arg-Ser-Arg-(Gly)$_n$ (n=0 SEQ ID NO:47; n=1 SEQ ID NO:48; n=2 SEQ ID NO:49; n=3 SEQ ID NO:50; n=4 SEQ ID NO:51; n=5 SEQ ID NO:52; n=6 SEQ ID NO:53).

28. A compound other than H-Lys-Arg-Ser-Arg-OH, H-Lys-Arg-Ala-Lys-OH, H-Lys-Arg-Ile-Lys-OH, H-Arg-Lys-Gly-Lys-OH, H-Arg-Lys-Ser-Arg-OH and H-Lys-Arg-Leu-Lys-OH of formula $$Aa^1\text{-}aa^2\text{-}aa^3\text{-}aa^4\text{-}(Gly)_n\text{—OH}$$

wherein:
Aa$^1$ represents the residue of an amino acid selected from the group consisting of H-Lys, H-Arg, H-Orn and 6-aminocaproic acid (Acp);
aa$^2$, and aa$^4$ independently represent the residue of an amino acid selected from the group consisting of lysine (Lys), arginine (Arg), and ornithine (Orn);
aa$^3$ represents the residue of an amino acid selected from the group consisting of alanine (Ala), glycine (Gly), valine (Val), leucine (Leu), isoleucine (Ile), serine (Ser), threonine (Thr), cysteine (Cys), methionine (Met), asparagine (Asn), norleucine (Nle), norvaline (Nva), and 2-aminobutyric acid (Abu); and n is zero or an integer from 1 to 6;
or pharmaceutically acceptable salt thereof.

29. A compound of formula

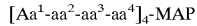

wherein:

Aa$^1$ represents the residue of an amino acid selected from the group consisting of H-Lys, H-Arg, H-Orn and 6-aminocaproic acid (Acp);

aa$^2$, and aa$^4$ independently represent the residue of an amino acid selected from the group consisting of lysine (Lys), arginine (Arg), and ornithine (Orn);

aa$^3$ represents the residue of an amino acid selected from the group consisting of alanine (Ala), glycine (Gly), valine (Val), leucine (Lcu), isoleucine (Ilc), serine (Ser), threonine (Thr), cysteine (Cys), methionine (Met), asparagine (Asn), norleucine (Nle), norvaline (Nva), and 2-aminobutyric acid (Abu);

MAP is a branched matrix of four lysine residues
or pharmaceutically acceptable salt thereof.

30. A method for promoting the adhesion of osteoblasts to a surface comprising:

(a) providing a peptide of molecular weight less than 4 kDa, other than SPPRRARVT, incorporating the sequence

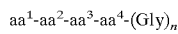

wherein:

aa$^1$ represents the residue of an amino acid selected from the group consisting of lysine (Lys), arginine (Arg), ornithine (Orn) and, when aa$^1$ is at the N-terminus, 6-aminocaproic acid (Acp);

aa$^2$, and aa$^4$ independently represent the residue of an amino acid selected from the group consisting of lysine (Lys), arginine (Arg), and ornithine (Orn);

aa$^3$ represents the residue of an amino acid selected from the group consisting of alanine (Ala), glycine (Gly), valine (Val), leucine (Leu), isoleucine (lie), serine (Ser), threonine (Thr), cysteine (Cys), methionine (Met) asparagine (Asn), norleucine (Nle), norvaline (Nva), and 2-aminobutyric acid (Abu); and n is zero or an integer from 1 to 6;

(b) applying said peptide to said surface; and (c) bringing osteoblasts into contact with said surface, whereby the adhesion of said osteoblasts to said surface is enhanced.

31. A biodegradable or inert polymer matrix which incorporates a compound of formula I or II:

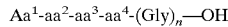     I

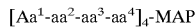     II wherein:

Aa$^1$ represents the residue of an amino acid selected from the group consisting of H-Lys, H-Arg, H-Orn and 6-aminocaproic acid (Acp);

aa$^2$, and aa$^4$ independently represent the residue of an amino acid selected from the group consisting of lysine (Lys), arginine (Arg), and ornithine (Orn);

aa3 represents the residue of an amino acid selected from the group consisting of alanine (Ala), glycine (Gly), valine (Val), leucine (Leu), isoleucine (lie), serine (Ser), threonine (Thr), cysteine (Cys), methionine (Met), asparagine (Asn), norleucine (Nle), norvaline (Nva), and 2-aminobutyric acid (Abu);

n is zero or an integer from 1to 6; and

MAP is a branched matrix of four lysine residues,
with the proviso that when Aa$^1$-aa$^2$-aa$^3$-aa$^4$-(Gly)$_n$—OH is Lys-Arg-Ser-Arg-(Gly)$_n$—OH, n cannot be zero.

32. A dimensionally stable biodegradable or inert polymer matrix which incorporates a compound of formula I or II:

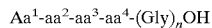     I

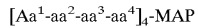     II wherein:

Aa$^1$ represents the residue of an amino acid selected from the group consisting of H-Lys, H-Arg, H-Orn and 6-aminocaproic acid (Acp);

aa$^2$, and aa$^4$ independently represent the residue of an amino acid selected from the group consisting of lysine (Lys), arginine (Arg), and ornithine (Orn);

aa$^3$ represents the residue of an amino acid selected from the group consisting of alanine (Ala), glycine (Gly), valine (Val), leucine (Leu), isoleucine (Ile), serine (Ser), threonine (Thr), cysteine (Cys), methionine (Met), asparagine (Asn), norleucine (Nle), norvaline (Nva), and 2-aminobutyric acid (Abu);

n is zero or an integer from 1 to 6; and

MAP is a branched matrix of four lysine residues.

33. A process for producing a bone replacement or bone-reconstructive material, the process comprising the steps of:

(a) preparing a biodegradable polymer matrix which incorporates a compound of formula I or II:

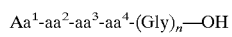     I

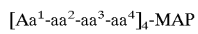     II wherein:

Aa$^1$ represents the residue of an amino acid selected from the group consisting of H-Lys, H-Arg, H-Orn and 6-aminocaproic acid (Acp);

aa$^2$, and aa$^4$ independently represent the residue of an amino acid selected from the group consisting of lysine (Lys), arginine (Arg), and ornithine (Orn);

aa$^3$ represents the residue of an amino acid selected from the group consisting of alanine (Ala), glycine (Gly), valine (Val), leucine (Leu), isoleucine (Ile), serine (Ser), threonine (Thr), cysteine (Cys), methionine (Met), asparagine (Asn), norleucine (Nle), norvaline (Nva), and 2-aminobutyric acid (Abu);

n is zero or an integer from 1 to 6; and

MAP is a branched matrix of four lysine residues; and (b) bringing osteoblasts into contact with the polymer matrix.

* * * * *

UNITED STATES PATENT AND TRADEMARK OFFICE
CERTIFICATE OF CORRECTION

PATENT NO. : 6,262,017 B1 Page 1 of 1
DATED : July 17, 2001
INVENTOR(S) : Dee et al.

It is certified that error appears in the above-identified patent and that said Letters Patent is hereby corrected as shown below:

<u>Column 40, claim 22,</u>
Line 51, delete "(Aep)" and insert -- (Acp) --

Signed and Sealed this

Fifth Day of March, 2002

*Attest:*

*Attesting Officer*

JAMES E. ROGAN
*Director of the United States Patent and Trademark Office*

SEQUENCE LISTING

```
(1) GENERAL INFORMATION:

(iii) NUMBER OF SEQUENCES: 53

(2) INFORMATION FOR SEQ ID NO: 1

(i) SEQUENCE CHARACTERISTICS:
        (A) LENGTH: 4 amino acids
        (B) TYPE: amino acid
        (D) TOPOLOGY: linear (ii) MOLECULE TYPE: peptide (iii) HYPOTHETICAL: no (vi) ORIGINAL SOURCE:

(xi) SEQUENCE DESCRIPTION: SEQ ID NO: 1:

Lys Arg Ser Arg
 1

(2) INFORMATION FOR SEQ ID NO: 2

(i) SEQUENCE CHARACTERISTICS:
        (A) LENGTH: 5 amino acids
        (B) TYPE: amino acid
        (D) TOPOLOGY: linear (ii) MOLECULE TYPE: peptide (iii) HYPOTHETICAL: yes (xi) SEQUENCE DESCRIPTION: SEQ ID NO: 2:

Lys Arg Ser Arg Gly
 1               5

(2) INFORMATION FOR SEQ ID NO: 3

(i) SEQUENCE CHARACTERISTICS:
        (A) LENGTH: 6 amino acids
        (B) TYPE: amino acid
        (D) TOPOLOGY: linear (ii) MOLECULE TYPE: peptide (iii) HYPOTHETICAL: yes (xi) SEQUENCE DESCRIPTION: SEQ ID NO: 3:

Lys Arg Ser Arg Gly Gly
 1               5

(2) INFORMATION FOR SEQ ID NO: 4

(i) SEQUENCE CHARACTERISTICS:
        (A) LENGTH: 7 amino acids
        (B) TYPE: amino acid
        (D) TOPOLOGY: linear (ii) MOLECULE TYPE: peptide (iii) HYPOTHETICAL: no (vi) ORIGINAL SOURCE:

(xi) SEQUENCE DESCRIPTION: SEQ ID NO: 4:

Lys Arg Ser Arg Gly Gly Gly
 1               5
```

(2) INFORMATION FOR SEQ ID NO: 5

(i) SEQUENCE CHARACTERISTICS:
        (A) LENGTH: 8 amino acids
        (B) TYPE: amino acid
        (D) TOPOLOGY: linear (ii) MOLECULE TYPE: peptide (iii) HYPOTHETICAL: yes (xi) SEQUENCE DESCRIPTION: SEQ ID NO: 5:

```
Lys Arg Ser Arg Gly Gly Gly Gly
1               5
```

(2) INFORMATION FOR SEQ ID NO: 6

(i) SEQUENCE CHARACTERISTICS:
        (A) LENGTH: 9 amino acids
        (B) TYPE: amino acid
        (D) TOPOLOGY: linear (ii) MOLECULE TYPE: peptide (iii) HYPOTHETICAL: yes (xi) SEQUENCE DESCRIPTION: SEQ ID NO: 6:

```
Lys Arg Ser Arg Gly Gly Gly Gly Gly
1               5
```

(2) INFORMATION FOR SEQ ID NO: 7

(i) SEQUENCE CHARACTERISTICS:
        (A) LENGTH: 10 amino acids
        (B) TYPE: amino acid
        (D) TOPOLOGY: linear (ii) MOLECULE TYPE: peptide (iii) HYPOTHETICAL: no (vi) ORIGINAL SOURCE:

(xi) SEQUENCE DESCRIPTION: SEQ ID NO: 7:

```
Lys Arg Ser Arg Gly Gly Gly Gly Gly Gly
1               5                   10
```

(2) INFORMATION FOR SEQ ID NO: 8

(i) SEQUENCE CHARACTERISTICS:
        (A) LENGTH: 4 amino acids
        (B) TYPE: amino acid
        (D) TOPOLOGY: linear (ii) MOLECULE TYPE: peptide (iii) HYPOTHETICAL: no (vi) ORIGINAL SOURCE:

(xi) SEQUENCE DESCRIPTION: SEQ ID NO: 8:

```
Arg Gly Asp Ser
1
```

(2) INFORMATION FOR SEQ ID NO: 9

(i) SEQUENCE CHARACTERISTICS:
        (A) LENGTH: 4 amino acids
        (B) TYPE: amino acid
        (D) TOPOLOGY: linear (ii) MOLECULE TYPE: peptide (iii) HYPOTHETICAL: no (vi) ORIGINAL SOURCE:

(xi) SEQUENCE DESCRIPTION: SEQ ID NO: 9:

Arg Asp Gly Ser
  1

(2) INFORMATION FOR SEQ ID NO: 10

(i) SEQUENCE CHARACTERISTICS:
             (A) LENGTH: 7 amino acids
             (B) TYPE: amino acid
             (D) TOPOLOGY: linear (ii) MOLECULE TYPE: peptide (iii) HYPOTHETICAL: no (vi) ORIGINAL SOURCE:

(xi) SEQUENCE DESCRIPTION: SEQ ID NO: 10:

Lys Ser Ser Arg Gly Gly Gly
  1               5

(2) INFORMATION FOR SEQ ID NO: 11

(i) SEQUENCE CHARACTERISTICS:
             (A) LENGTH: 4 amino acids
             (B) TYPE: amino acid
             (D) TOPOLOGY: linear (ii) MOLECULE TYPE: peptide (iii) HYPOTHETICAL: no (vi) ORIGINAL SOURCE:

(xi) SEQUENCE DESCRIPTION: SEQ ID NO: 11

His His Trp His
  1

(2) INFORMATION FOR SEQ ID NO: 12

(i) SEQUENCE CHARACTERISTICS:
             (A) LENGTH: 4 amino acids
             (B) TYPE: amino acid
             (D) TOPOLOGY: linear (ii) MOLECULE TYPE: peptide (iii) HYPOTHETICAL: yes (xi) SEQUENCE DESCRIPTION: SEQ ID NO: 12

Lys Arg Met Arg
  1

(2) INFORMATION FOR SEQ ID NO: 13

(i) SEQUENCE CHARACTERISTICS:
             (A) LENGTH: 5 amino acids
             (B) TYPE: amino acid
             (D) TOPOLOGY: linear (ii) MOLECULE TYPE: peptide (iii) HYPOTHETICAL: yes (xi) SEQUENCE DESCRIPTION: SEQ ID NO: 13

Lys Arg Met Arg Gly
1               5

(2) INFORMATION FOR SEQ ID NO: 14

(i) SEQUENCE CHARACTERISTICS:
        (A) LENGTH: 6 amino acids
        (B) TYPE: amino acid
        (D) TOPOLOGY: linear (ii) MOLECULE TYPE: peptide (iii) HYPOTHETICAL: yes (xi) SEQUENCE DESCRIPTION: SEQ ID NO: 14

Lys Arg Met Arg Gly Gly
1               5

(2) INFORMATION FOR SEQ ID NO: 15

(i) SEQUENCE CHARACTERISTICS:
        (A) LENGTH: 7 amino acids
        (B) TYPE: amino acid
        (D) TOPOLOGY: linear (ii) MOLECULE TYPE: peptide (iii) HYPOTHETICAL: yes (xi) SEQUENCE DESCRIPTION: SEQ ID NO: 15

Lys Arg Met Arg Gly Gly Gly
1               5

(2) INFORMATION FOR SEQ ID NO: 16

(i) SEQUENCE CHARACTERISTICS:
        (A) LENGTH: 8 amino acids
        (B) TYPE: amino acid
        (D) TOPOLOGY: linear (ii) MOLECULE TYPE: peptide (iii) HYPOTHETICAL: yes (xi) SEQUENCE DESCRIPTION: SEQ ID NO: 16

Lys Arg Met Arg Gly Gly Gly Gly
1               5

(2) INFORMATION FOR SEQ ID NO: 17

(i) SEQUENCE CHARACTERISTICS:
        (A) LENGTH: 9 amino acids
        (B) TYPE: amino acid
        (D) TOPOLOGY: linear (ii) MOLECULE TYPE: peptide (iii) HYPOTHETICAL: yes (xi) SEQUENCE DESCRIPTION: SEQ ID NO: 17

Lys Arg Met Arg Gly Gly Gly Gly Gly
1               5

(2) INFORMATION FOR SEQ ID NO: 18

(i) SEQUENCE CHARACTERISTICS:
        (A) LENGTH: 10 amino acids
        (B) TYPE: amino acid

```
        (D) TOPOLOGY: linear (ii) MOLECULE TYPE: peptide (iii) HYPOTHETICAL: yes (xi) SEQUENCE DESCRIPTION: SEQ ID NO: 18

Lys Arg Met Arg Gly Gly Gly Gly Gly
1               5                   10

(2) INFORMATION FOR SEQ ID NO: 19

(i) SEQUENCE CHARACTERISTICS:
        (A) LENGTH: 4 amino acids
        (B) TYPE: amino acid
        (D) TOPOLOGY: linear (ii) MOLECULE TYPE: peptide (iii) HYPOTHETICAL: yes (xi) SEQUENCE DESCRIPTION: SEQ ID NO: 19

Lys Arg Ala Arg
1

(2) INFORMATION FOR SEQ ID NO: 20

(i) SEQUENCE CHARACTERISTICS:
        (A) LENGTH: 5 amino acids
        (B) TYPE: amino acid
        (D) TOPOLOGY: linear (ii) MOLECULE TYPE: peptide (iii) HYPOTHETICAL: yes (xi) SEQUENCE DESCRIPTION: SEQ ID NO: 20

Lys Arg Ala Arg Gly
1               5

(2) INFORMATION FOR SEQ ID NO: 21

(i) SEQUENCE CHARACTERISTICS:
        (A) LENGTH: 6 amino acids
        (B) TYPE: amino acid
        (D) TOPOLOGY: linear (ii) MOLECULE TYPE: peptide (iii) HYPOTHETICAL: yes (xi) SEQUENCE DESCRIPTION: SEQ ID NO: 21

Lys Arg Ala Arg Gly Gly
1               5

(2) INFORMATION FOR SEQ ID NO: 22

(i) SEQUENCE CHARACTERISTICS:
        (A) LENGTH: 7 amino acids
        (B) TYPE: amino acid
        (D) TOPOLOGY: linear (ii) MOLECULE TYPE: peptide (iii) HYPOTHETICAL: yes (xi) SEQUENCE DESCRIPTION: SEQ ID NO: 22

Lys Arg Ala Arg Gly Gly Gly
1               5
```

(2) INFORMATION FOR SEQ ID NO: 23

(i) SEQUENCE CHARACTERISTICS:
        (A) LENGTH: 8 amino acids
        (B) TYPE: amino acid
        (D) TOPOLOGY: linear (ii) MOLECULE TYPE: peptide (iii) HYPOTHETICAL: yes (xi) SEQUENCE DESCRIPTION: SEQ ID NO: 23

```
Lys Arg Ala Arg Gly Gly Gly Gly
1               5
```

(2) INFORMATION FOR SEQ ID NO: 24

(i) SEQUENCE CHARACTERISTICS:
        (A) LENGTH: 9 amino acids
        (B) TYPE: amino acid
        (D) TOPOLOGY: linear (ii) MOLECULE TYPE: peptide (iii) HYPOTHETICAL: yes (xi) SEQUENCE DESCRIPTION: SEQ ID NO: 24

```
Lys Arg Ala Arg Gly Gly Gly Gly Gly
1               5
```

(2) INFORMATION FOR SEQ ID NO: 25

(i) SEQUENCE CHARACTERISTICS:
        (A) LENGTH: 10 amino acids
        (B) TYPE: amino acid
        (D) TOPOLOGY: linear (ii) MOLECULE TYPE: peptide (iii) HYPOTHETICAL: yes (xi) SEQUENCE DESCRIPTION: SEQ ID NO: 25

```
Lys Arg Ala Arg Gly Gly Gly Gly Gly Gly
1               5                   10
```

(2) INFORMATION FOR SEQ ID NO: 26

(i) SEQUENCE CHARACTERISTICS:
        (A) LENGTH: 4 amino acids
        (B) TYPE: amino acid
        (D) TOPOLOGY: linear (ii) MOLECULE TYPE: peptide (iii) HYPOTHETICAL: yes (xi) SEQUENCE DESCRIPTION: SEQ ID NO: 26

```
Arg Arg Ser Arg
1
```

(2) INFORMATION FOR SEQ ID NO: 27

(i) SEQUENCE CHARACTERISTICS:
        (A) LENGTH: 5 amino acids
        (B) TYPE: amino acid
        (D) TOPOLOGY: linear (ii) MOLECULE TYPE: peptide (iii) HYPOTHETICAL: yes (xi) SEQUENCE DESCRIPTION: SEQ ID NO: 27

Arg Arg Ser Arg Gly
1               5

(2) INFORMATION FOR SEQ ID NO: 28

(i) SEQUENCE CHARACTERISTICS:
            (A) LENGTH: 6 amino acids
            (B) TYPE: amino acid
            (D) TOPOLOGY: linear (ii) MOLECULE TYPE: peptide (iii) HYPOTHETICAL: yes (xi) SEQUENCE DESCRIPTION: SEQ ID NO: 28

Arg Arg Ser Arg Gly Gly
1               5

(2) INFORMATION FOR SEQ ID NO: 29

(i) SEQUENCE CHARACTERISTICS:
            (A) LENGTH: 7 amino acids
            (B) TYPE: amino acid
            (D) TOPOLOGY: linear (ii) MOLECULE TYPE: peptide (iii) HYPOTHETICAL: yes (xi) SEQUENCE DESCRIPTION: SEQ ID NO: 29

Arg Arg Ser Arg Gly Gly Gly
1               5

(2) INFORMATION FOR SEQ ID NO: 30

(i) SEQUENCE CHARACTERISTICS:
            (A) LENGTH: 8 amino acids
            (B) TYPE: amino acid
            (D) TOPOLOGY: linear (ii) MOLECULE TYPE: peptide (iii) HYPOTHETICAL: yes (xi) SEQUENCE DESCRIPTION: SEQ ID NO: 30

Arg Arg Ser Arg Gly Gly Gly Gly
1               5

(2) INFORMATION FOR SEQ ID NO: 31

(i) SEQUENCE CHARACTERISTICS:
            (A) LENGTH: 9 amino acids
            (B) TYPE: amino acid
            (D) TOPOLOGY: linear (ii) MOLECULE TYPE: peptide (iii) HYPOTHETICAL: yes (xi) SEQUENCE DESCRIPTION: SEQ ID NO: 31

Arg Arg Ser Arg Gly Gly Gly Gly Gly
1               5

(2) INFORMATION FOR SEQ ID NO: 32

(i) SEQUENCE CHARACTERISTICS:
            (A) LENGTH: 10 amino acids

```
          (B) TYPE: amino acid
          (D) TOPOLOGY: linear (ii) MOLECULE TYPE: peptide (iii) HYPOTHETICAL: yes (xi) SEQUENCE DESCRIPTION: SEQ ID NO: 32

Arg Arg Ser Arg Gly Gly Gly Gly Gly Gly
1               5                   10

(2) INFORMATION FOR SEQ ID NO: 33

(i) SEQUENCE CHARACTERISTICS:
          (A) LENGTH: 4 amino acids
          (B) TYPE: amino acid
          (D) TOPOLOGY: linear (ii) MOLECULE TYPE: peptide (iii) HYPOTHETICAL: yes (ix) FEATURE:
          (D) OTHER INFORMATION:  Xaa at position 1 is Orn (xi) SEQUENCE DESCRIPTION: SEQ ID NO: 33

Xaa Arg Ser Arg
1

(2) INFORMATION FOR SEQ ID NO: 34

(i) SEQUENCE CHARACTERISTICS:
          (A) LENGTH: 5 amino acids
          (B) TYPE: amino acid
          (D) TOPOLOGY: linear (ii) MOLECULE TYPE: peptide (iii) HYPOTHETICAL: yes (ix) FEATURE:
          (D) OTHER INFORMATION:  Xaa at position 1 is Orn (xi) SEQUENCE DESCRIPTION: SEQ ID NO: 34

Xaa Arg Ser Arg Gly
1               5

(2) INFORMATION FOR SEQ ID NO: 35

(i) SEQUENCE CHARACTERISTICS:
          (A) LENGTH: 6 amino acids
          (B) TYPE: amino acid
          (D) TOPOLOGY: linear (ii) MOLECULE TYPE: peptide (iii) HYPOTHETICAL: yes (ix) FEATURE:
          (D) OTHER INFORMATION:  Xaa at position 1 is Orn (xi) SEQUENCE DESCRIPTION: SEQ ID NO: 35

Xaa Arg Ser Arg Gly Gly
1               5

(2) INFORMATION FOR SEQ ID NO: 36

(i) SEQUENCE CHARACTERISTICS:
          (A) LENGTH: 7 amino acids
          (B) TYPE: amino acid
          (D) TOPOLOGY: linear
```

```
        (ii) MOLECULE TYPE: peptide (iii) HYPOTHETICAL: yes (ix) FEATURE:
               (D) OTHER INFORMATION:  Xaa at position 1 is Orn (xi) SEQUENCE DESCRIPTION: SEQ ID NO: 36

Xaa Arg Ser Arg Gly Gly Gly
  1               5

(2) INFORMATION FOR SEQ ID NO: 37

(i) SEQUENCE CHARACTERISTICS:
              (A) LENGTH: 8 amino acids
              (B) TYPE: amino acid
              (D) TOPOLOGY: linear (ii) MOLECULE TYPE: peptide (iii) HYPOTHETICAL: yes (ix) FEATURE:
               (D) OTHER INFORMATION:  Xaa at position 1 is Orn (xi) SEQUENCE DESCRIPTION: SEQ ID NO: 37

Xaa Arg Ser Arg Gly Gly Gly Gly
  1               5

(2) INFORMATION FOR SEQ ID NO: 38

(i) SEQUENCE CHARACTERISTICS:
              (A) LENGTH: 9 amino acids
              (B) TYPE: amino acid
              (D) TOPOLOGY: linear (ii) MOLECULE TYPE: peptide (iii) HYPOTHETICAL: yes (ix) FEATURE:
               (D) OTHER INFORMATION:  Xaa at position 1 is Orn (xi) SEQUENCE DESCRIPTION: SEQ ID NO: 38

Xaa Arg Ser Arg Gly Gly Gly Gly Gly
  1               5

(2) INFORMATION FOR SEQ ID NO: 39

(i) SEQUENCE CHARACTERISTICS:
              (A) LENGTH: 10 amino acids
              (B) TYPE: amino acid
              (D) TOPOLOGY: linear (ii) MOLECULE TYPE: peptide (iii) HYPOTHETICAL: yes (ix) FEATURE:
               (D) OTHER INFORMATION:  Xaa at position 1 is Orn (xi) SEQUENCE DESCRIPTION: SEQ ID NO: 39

Xaa Arg Ser Arg Gly Gly Gly Gly Gly Gly
  1               5                  10

(2) INFORMATION FOR SEQ ID NO: 40

(i) SEQUENCE CHARACTERISTICS:
              (A) LENGTH: 4 amino acids
              (B) TYPE: amino acid
```

(D) TOPOLOGY: linear (ii) MOLECULE TYPE: peptide (iii) HYPOTHETICAL: yes (xi) SEQUENCE DESCRIPTION: SEQ ID NO: 40

Lys Lys Ser Lys
 1

(2) INFORMATION FOR SEQ ID NO: 41

(i) SEQUENCE CHARACTERISTICS:
            (A) LENGTH: 5 amino acids
            (B) TYPE: amino acid
            (D) TOPOLOGY: linear (ii) MOLECULE TYPE: peptide (iii) HYPOTHETICAL: yes (xi) SEQUENCE DESCRIPTION: SEQ ID NO: 41

Lys Lys Ser Lys Gly
 1               5

(2) INFORMATION FOR SEQ ID NO: 42

(i) SEQUENCE CHARACTERISTICS:
            (A) LENGTH: 6 amino acids
            (B) TYPE: amino acid
            (D) TOPOLOGY: linear (ii) MOLECULE TYPE: peptide (iii) HYPOTHETICAL: yes (xi) SEQUENCE DESCRIPTION: SEQ ID NO: 42

Lys Lys Ser Lys Gly Gly
 1               5

(2) INFORMATION FOR SEQ ID NO: 43

(i) SEQUENCE CHARACTERISTICS:
            (A) LENGTH: 7 amino acids
            (B) TYPE: amino acid
            (D) TOPOLOGY: linear (ii) MOLECULE TYPE: peptide (iii) HYPOTHETICAL: yes (xi) SEQUENCE DESCRIPTION: SEQ ID NO: 43

Lys Lys Ser Lys Gly Gly Gly
 1               5

(2) INFORMATION FOR SEQ ID NO: 44

(i) SEQUENCE CHARACTERISTICS:
            (A) LENGTH: 8 amino acids
            (B) TYPE: amino acid
            (D) TOPOLOGY: linear (ii) MOLECULE TYPE: peptide (iii) HYPOTHETICAL: yes (xi) SEQUENCE DESCRIPTION: SEQ ID NO: 44

Lys Lys Ser Lys Gly Gly Gly Gly
 1               5

(2) INFORMATION FOR SEQ ID NO: 45

(i) SEQUENCE CHARACTERISTICS:
        (A) LENGTH: 9 amino acids
        (B) TYPE: amino acid
        (D) TOPOLOGY: linear (ii) MOLECULE TYPE: peptide (iii) HYPOTHETICAL: yes (xi) SEQUENCE DESCRIPTION: SEQ ID NO: 45

Lys Lys Ser Lys Gly Gly Gly Gly Gly
 1               5

(2) INFORMATION FOR SEQ ID NO: 46

(i) SEQUENCE CHARACTERISTICS:
        (A) LENGTH: 10 amino acids
        (B) TYPE: amino acid
        (D) TOPOLOGY: linear (ii) MOLECULE TYPE: peptide (iii) HYPOTHETICAL: yes (xi) SEQUENCE DESCRIPTION: SEQ ID NO: 46

Lys Lys Ser Lys Gly Gly Gly Gly Gly Gly
 1               5                   10

(2) INFORMATION FOR SEQ ID NO: 47

(i) SEQUENCE CHARACTERISTICS:
        (A) LENGTH: 4 amino acids
        (B) TYPE: amino acid
        (D) TOPOLOGY: linear (ii) MOLECULE TYPE: peptide (iii) HYPOTHETICAL: yes (ix) FEATURE:
        (D) OTHER INFORMATION:  Xaa at position 1 is Acp (xi) SEQUENCE DESCRIPTION: SEQ ID NO: 47

Xaa Arg Ser Arg
 1

(2) INFORMATION FOR SEQ ID NO: 48

(i) SEQUENCE CHARACTERISTICS:
        (A) LENGTH: 5 amino acids
        (B) TYPE: amino acid
        (D) TOPOLOGY: linear
            38.1

(ii) MOLECULE TYPE: peptide (iii) HYPOTHETICAL: yes (ix) FEATURE:
        (D) OTHER INFORMATION:  Xaa at position 1 is Acp (xi) SEQUENCE DESCRIPTION: SEQ ID NO: 48

Xaa Arg Ser Arg Gly
 1               5

(2) INFORMATION FOR SEQ ID NO: 49

(i) SEQUENCE CHARACTERISTICS:

(A) LENGTH: 6 amino acids
            (B) TYPE: amino acid
            (D) TOPOLOGY: linear (ii) MOLECULE TYPE: peptide (iii) HYPOTHETICAL: yes (ix) FEATURE:
            (D) OTHER INFORMATION:  Xaa at position 1 is Acp (xi) SEQUENCE DESCRIPTION: SEQ ID NO: 49

Xaa Arg Ser Arg Gly Gly
 1               5

(2) INFORMATION FOR SEQ ID NO: 50

(i) SEQUENCE CHARACTERISTICS:
            (A) LENGTH: 7 amino acids
            (B) TYPE: amino acid
            (D) TOPOLOGY: linear (ii) MOLECULE TYPE: peptide (iii) HYPOTHETICAL: yes (ix) FEATURE:
            (D) OTHER INFORMATION:  Xaa at position 1 is Acp (xi) SEQUENCE DESCRIPTION: SEQ ID NO: 50

Xaa Arg Ser Arg Gly Gly Gly
 1               5

(2) INFORMATION FOR SEQ ID NO: 51

(i) SEQUENCE CHARACTERISTICS:
            (A) LENGTH: 8 amino acids
            (B) TYPE: amino acid
            (D) TOPOLOGY: linear (ii) MOLECULE TYPE: peptide (iii) HYPOTHETICAL: yes (ix) FEATURE:
            (D) OTHER INFORMATION:  Xaa at position 1 is Acp (xi) SEQUENCE DESCRIPTION: SEQ ID NO: 51

Xaa Arg Ser Arg Gly Gly Gly Gly
 1               5

(2) INFORMATION FOR SEQ ID NO: 52

(i) SEQUENCE CHARACTERISTICS:
            (A) LENGTH: 9 amino acids
            (B) TYPE: amino acid
            (D) TOPOLOGY: linear (ii) MOLECULE TYPE: peptide (iii) HYPOTHETICAL: yes
                38.2

(ix) FEATURE:
            (D) OTHER INFORMATION:  Xaa at position 1 is Acp (xi) SEQUENCE DESCRIPTION: SEQ ID NO: 52

Xaa Arg Ser Arg Gly Gly Gly Gly Gly
 1               5

(2) INFORMATION FOR SEQ ID NO: 53

```
    (i) SEQUENCE CHARACTERISTICS:
        (A) LENGTH: 10 amino acids
        (B) TYPE: amino acid
        (D) TOPOLOGY: linear (ii) MOLECULE TYPE: peptide (iii) HYPOTHETICAL: yes (ix) FEATURE:
        (D) OTHER INFORMATION:   Xaa at position 1 is Acp (xi) SEQUENCE DESCRIPTION: SEQ ID NO: 53

Xaa Arg Ser Arg Gly Gly Gly Gly Gly Gly
 1               5                   10
```